US010039439B2

(12) United States Patent
Aoyama

(10) Patent No.: US 10,039,439 B2
(45) Date of Patent: Aug. 7, 2018

(54) ENDOSCOPE SYSTEM AND METHOD FOR OPERATING THE SAME

(71) Applicant: FUJIFILM Corporation, Tokyo (JP)

(72) Inventor: Tatsuya Aoyama, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 366 days.

(21) Appl. No.: 14/869,285

(22) Filed: Sep. 29, 2015

(65) Prior Publication Data
US 2016/0089012 A1    Mar. 31, 2016

(30) Foreign Application Priority Data

Sep. 30, 2014 (JP) .................................. 2014-202646
Sep. 30, 2014 (JP) .................................. 2014-202647

(51) Int. Cl.
*A61B 1/06* (2006.01)
*H04N 5/225* (2006.01)
(Continued)

(52) U.S. Cl.
CPC .......... *A61B 1/0638* (2013.01); *G06T 7/0012* (2013.01); *H04N 5/2256* (2013.01); *H04N 5/2354* (2013.01); *H04N 9/045* (2013.01); *A61B 1/04* (2013.01); *A61B 1/0646* (2013.01); *A61B 1/0684* (2013.01); *G06T 2207/10024* (2013.01); *G06T 2207/10068* (2013.01);
(Continued)

(58) Field of Classification Search
CPC .................................................. A61B 1/0638
See application file for complete search history.

(56) References Cited

U.S. PATENT DOCUMENTS

2012/0190922 A1    7/2012   Kaku
2015/0363932 A1    12/2015  Hirota et al.

FOREIGN PATENT DOCUMENTS

JP      2012-170639 A    9/2012
JP      2012170639    *   9/2012 ............... A61B 1/00
(Continued)

OTHER PUBLICATIONS

Osareh et al., "An Automated Tracking Approach for Extraction of Retinal Vasculature in Fundus Images", Journal of Ophthalmic and Vision Research, vol. 5, No. 1, Jan. 2010, 6 pages.
(Continued)

*Primary Examiner* — James Pontius
(74) *Attorney, Agent, or Firm* — Birch, Stewart, Kolasch & Birch, LLP

(57) ABSTRACT

An endoscope system is provided with a light source unit for generating illumination light, an image sensor for imaging an object of interest irradiated with the illumination light, an image signal obtaining section, a calculated image signal generator, and an image generator. The image signal obtaining section obtains a B1 image signal corresponding to violet light and a B2 image signal corresponding to blue light. The calculated image signal generator generates a calculated image signal from the B1 and B2 image signals. The image generator generates an image in which one of the B1 image signal and the B2 image signal is assigned to a luminance channel or a green channel and the calculated image signal is assigned to a remaining channel.

19 Claims, 11 Drawing Sheets

(51) Int. Cl.
　　　*G06T 7/00*　　　　(2017.01)
　　　*H04N 5/235*　　　(2006.01)
　　　*H04N 9/04*　　　　(2006.01)
　　　*A61B 1/04*　　　　(2006.01)

(52) U.S. Cl.
　　　CPC ............... *G06T 2207/20212* (2013.01); *G06T 2207/30101* (2013.01); *H04N 2005/2255* (2013.01)

(56) References Cited

FOREIGN PATENT DOCUMENTS

| | | |
|---|---|---|
| JP | 2013-144039 A | 7/2013 |
| JP | 2013-255808 A | 12/2013 |
| JP | 5393525 B2 | 1/2014 |
| JP | 5435746 B2 | 3/2014 |
| JP | 2014-161627 A | 9/2014 |

OTHER PUBLICATIONS

Japanese Office Action, dated Nov. 2, 2016, for Japanese Application No. 2014-202646, together with an English translation thereof.
Japanese Office Action, dated Nov. 2, 2016, for Japanese Application No. 2014-202647, together with an English translation thereof.

\* cited by examiner

ENDOSCOPE SYSTEM AND METHOD FOR OPERATING THE SAME

CROSS-REFERENCE TO RELATED APPLICATIONS

The present application claims priority under 35 U.S.C. § 119 to Japanese Patent Application No. 2014-202646, filed Sep. 30, 2014 and Japanese Patent Application No. 2014-202647, filed Sep. 30, 2014. Each of the above application(s) is hereby expressly incorporated by reference, in its entirety, into the present application.

BACKGROUND OF THE INVENTION

1. Field of the Invention

The present invention relates to an endoscope system for extracting blood vessels of an object of interest from image signals generated by imaging the object of interest and a method for operating an endoscope system.

2. Description Related to the Prior Art

In medical fields, diagnoses using endoscope systems are widely performed. The endoscope system comprises a light source device, an endoscope system, and a processor device. To perform diagnostic endoscopy using the endoscope system, an insertion section of the endoscope is inserted into a body cavity and illumination light is applied to an object of interest (hereinafter referred to as the object) through a distal portion of the insertion section. An image sensor provided in the distal portion captures an image of the object irradiated with the illumination light and generates image signals. An image of the object is produced from the image signals and displayed on a monitor.

The shape and the distribution of blood vessels are important in diagnoses using the endoscope system. The endoscope systems that extract the blood vessels through various methods have been known recently. For example, an endoscope system that extracts the blood vessels through pattern matching has been known (see US2012/0190922 (corresponding to Japanese Patent No. 05435746) and Japanese Patent Unexamined Publication No. 2013-255808). Also, methods for extracting blood vessels with the use of a Gabor filter, a neural network, or the like have been known (see An Automated Tracking Approach for Extraction of Retinal Vasculature in Fundus Images, A. Osareh et al., J Ophthalmic Vis Res 2010; 5 (1): 20-26). There has been known an endoscope system that assigns weights to the images generated by using blue narrowband light and green narrowband light, respectively. Thereby the endoscope system extracts blood vessels (hereinafter referred to as the surface blood vessels) located in a relatively shallow position under the mucosal surface and blood vessels (hereinafter may referred to as the subsurface blood vessels) located in deep positions in a medium depth layer and a deep layer under the mucosal surface (see Japanese Patent No. 5393525).

Recently, it has been known that information about blood vessels located at a specific depth in addition to the information about the presence and absence of the blood vessels is used for determining the staging of a disease (e.g. cancer or the like). For example, the blood vessel density at a specific depth is used for determining the staging of superficial cancer of digestive tract. More specifically, for example, the blood vessel density of blood vessels (hereinafter referred to as the superficial blood vessels) that are located in an especially shallow position under the mucosal surface and included in the surface blood vessels located in the proximity of the mucosal surface, varies significantly as Barrett's esophagus progresses to Barrett's adenocarcinoma. For this reason, it has been considered that the staging accuracy is improved by enhancing and displaying the superficial blood vessels or by calculating the blood vessel density of the superficial blood vessels.

In a method for extracting and enhancing blood vessels with a conventional endoscope system, the penetration depth of the illumination light applied to the object in imaging determines the approximate depth of the blood vessels rendered observable. For example, the illumination light having shorter wavelengths such as blue light or violet light renders the surface blood vessels observable. However, it is the density of the superficial blood vessels that varies significantly between the stages of the Barrett's adenocarcinoma. The staging accuracy of the Barrett's adenocarcinoma is reduced by superimposing the blood vessels located in the entire surface layer, which is wide in the depth direction, with each other as in the conventional method, even if the blood vessels include the superficial blood vessels.

The endoscope system described in the Japanese Patent No. 5393525 is capable of extracting the surface blood vessels or the subsurface blood vessels through assigning two types of weights to the respective images because there is a large difference in depth between the surface blood vessels and the subsurface blood vessels. It is difficult for this method to extract the superficial blood vessels from the surface blood vessels. Even if the extraction of the superficial blood vessels may be attempted by assigning the two types of weights to the images, the balance of the weighting is extremely rigorous. In addition, there are individual differences between the objects. Thus, it is difficult to extract only the superficial blood vessels from the surface blood vessels with stability.

SUMMARY OF THE INVENTION

An object of the present invention is to provide an endoscope system for extracting and displaying blood vessels located in a region in a specific direction (hereinafter referred to as the specific depth) and a method for operating an endoscope system.

An aspect of the present invention provides an endoscope system comprising a light source unit, an image sensor, an image signal obtaining section, a calculated image signal generator, and an image generator. The light source unit generates illumination light. The image sensor images an object of interest irradiated with the illumination light. The image signal obtaining section obtains a first image signal and a second image signal from the image sensor. The first image signal corresponds to first illumination light of the illumination light. The second image signal corresponds to second illumination light of the illumination light. The second illumination light is different in wavelength range from the first illumination light. The calculated image signal generator generates a calculated image signal through calculation using the first image signal and the second image signal. The image generator generates an image in which one of the first image signal and the second image signal is assigned to a luminance channel or a green channel and the calculated image signal is assigned to a remaining channel.

It is preferred that the light source unit sequentially generates the first illumination light and the second illumination light having wavelengths longer than the first illumination light.

It is preferred that the image generator assigns the calculated image signal to two chrominance channels in a case where the image generator assigns one of the first and second image signals to the luminance channel, and the image generator assigns the calculated image signal to a red channel and a blue channel in a case where the image generator assigns one of the first and second image signals to the green channel.

It is preferred that the calculated image signal generator generates the calculated image signal that represents a running pattern of blood vessels located at a specific depth in the object, density of the blood vessels, or an oxygen saturation level of the blood vessels.

It is preferred that the calculated image signal generator calculates a ratio or a difference between the first image signal and the second image signal to generate the calculated image signal.

It is preferred that the endoscope system further comprises a resolution reduction processor for performing a resolution reduction process to reduce resolution of the calculated image signal. It is preferred that the image generator assigns the calculated image signal with the resolution reduced by the resolution reduction processor to the remaining channel.

It is preferred that the endoscope system further comprises an image registration processor for correcting at least one of the first image signal and the second image signal and for performing registration between the object represented by the first image signal and the object represented by the second image signal. It is preferred that the calculated image signal generator generates the calculated image signal from the first and second image signals in which the registration of the objects has been performed by the image registration processor.

It is preferred that the resolution reduction processor sets magnitude of the resolution reduction process in accordance with accuracy of the registration performed by the image registration processor.

It is preferred that the resolution reduction processor reduces the magnitude of the resolution reduction process as the accuracy of the registration performed by the image registration processor is increased.

It is preferred that the image registration processor sets accuracy of the registration in accordance with magnitude of the resolution reduction process performed by the resolution reduction processor.

It is preferred that the image registration processor increases the accuracy of the registration as the magnitude of the resolution reduction process performed by the resolution reduction processor is reduced.

It is preferred that the image registration processor sets accuracy of the registration low and the resolution reduction processor sets magnitude of the registration reduction process high in a case where the image generated by the image generator is displayed as a movie, as compared to the accuracy and the magnitude in a case where the image generated by the image generator is displayed or stored as a still image.

It is preferred that the image registration processor sets accuracy of the registration high and the resolution reduction processor sets magnitude of the registration reduction process low in a case where the image generated by the image generator is stored as a still image, as compared to the accuracy and the magnitude in a case where the image generated by the image generator is displayed as a movie.

It is preferred that the endoscope system further comprises a brightness correction processor for correcting brightness of at least one of the first image signal and the second image signal. It is preferred that the image generator generates the image from the first or second image signal with the brightness corrected by the brightness correction processor.

It is preferred that the image generator assigns one of the first and second image signals with less noise to the luminance channel or the green channel.

It is preferred that the image generator assigns one of the first and second image signals with higher contrast to the luminance channel or the green channel.

It is preferred that the image generator has a first mode, in which the first image signal is assigned to the luminance channel or the green channel, and a second mode, in which the second image signal is assigned to the luminance channel or the green channel, and the image generator generates the image in the first mode or the second mode selected.

It is preferred that the image generator assigns the first image signal to the luminance channel or the green channel in a case where the first illumination light has wavelengths shorter than the second illumination light, and assigns the second image signal to the luminance channel or the green channel in a case where the second illumination light has wavelengths shorter than the first illumination light.

It is preferred that the center wavelength of the first illumination light is 405±10 nm and the center wavelength of the second illumination light is 445±10 nm.

An aspect of the present invention provides a method for operating an endoscope system comprising a light generating step, an imaging step, an obtaining step, a signal generating step, and an image generating step. In the light generating step, a light source unit generates illumination light. In the imaging step, an image sensor images an object of interest irradiated with the illumination light. In the obtaining step, an image signal obtaining section obtains a first image signal and a second image signal from the image sensor. The first image signal corresponds to first illumination light of the illumination light. The second image signal corresponds to second illumination light of the illumination light. The second illumination light is different in wavelength range from the first illumination light. In the signal generating step, a calculated image signal generator generates a calculated image signal through calculation using the first image signal and the second image signal. In the image generating step, image generator generates an image in which one of the first image signal and the second image signal is assigned to a luminance channel or a green channel and the calculated image signal is assigned to a remaining channel.

Thus, the aspects of the present invention provide an endoscope system for extracting and displaying blood vessels located at a specific depth and a method for operating an endoscope system.

BRIEF DESCRIPTION OF THE DRAWINGS

The above and other objects and advantages of the present invention will be more apparent from the following detailed description of the preferred embodiments when read in connection with the accompanied drawings, wherein like reference numerals designate like or corresponding parts throughout the several views, and wherein.

DESCRIPTION OF THE PREFERRED EMBODIMENTS

Figure 1:
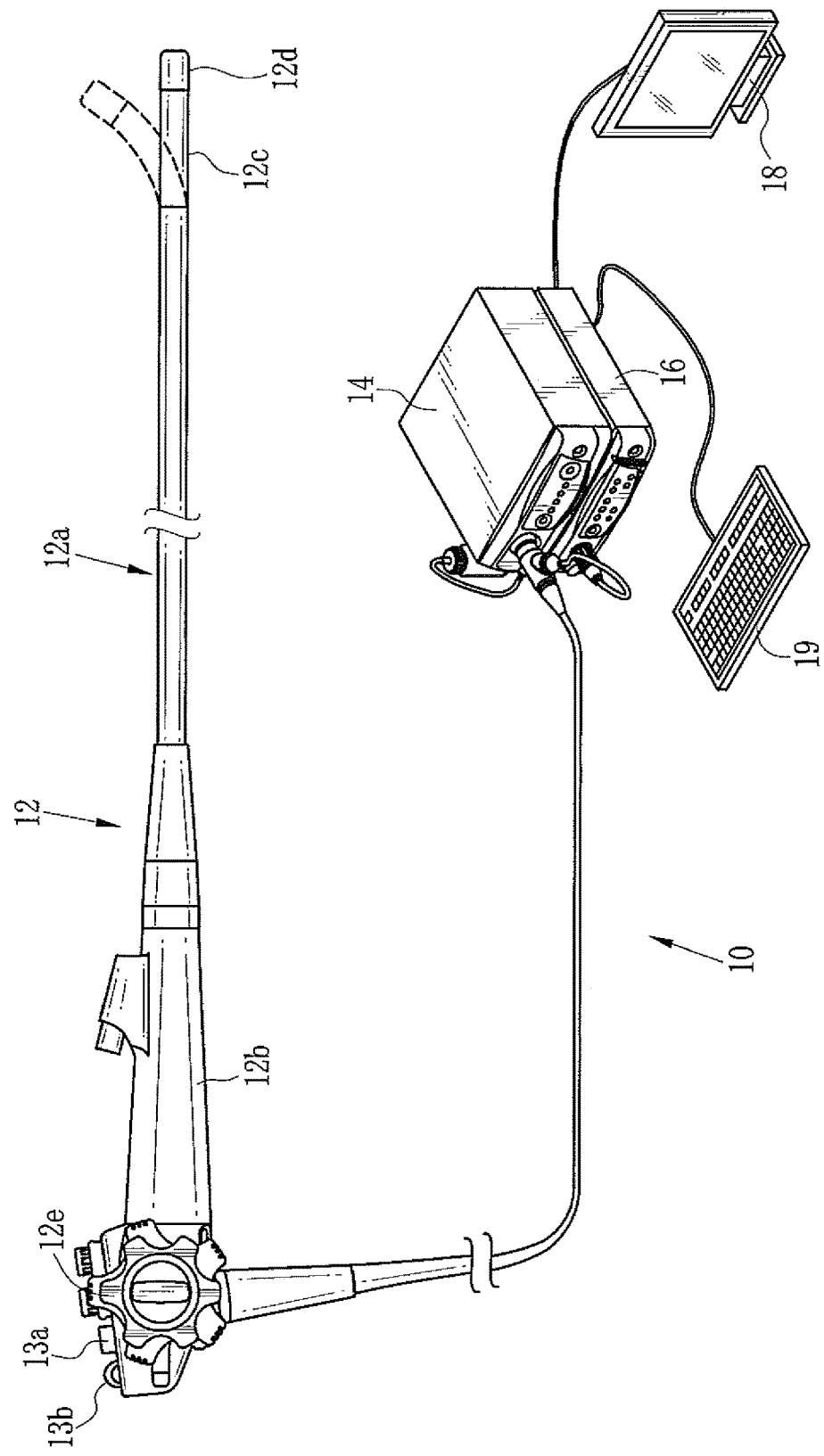
FIG. 1 is an external view of an endoscope system.

In FIG. 1, an endoscope system 10 comprises an endoscope 12, a light source device 14, a processor device 16, a monitor 18, and a console 19. The endoscope 12 is connected optically to the light source device 14 and electrically to the processor device 16. The endoscope 12 comprises an insertion section 12a to be inserted into a body cavity, a control handle unit 12b provided at the proximal end of the insertion section 12a, a flexible portion 12c, and a distal portion 12d. The distal portion 12d is coupled to the flexible portion 12c, which is provided on the distal side of the insertion section 12a. The flexible portion 12c is bent by operating an angle knob 12e of the control handle unit 12b. The distal portion 12d is directed to a desired direction by bending the flexible portion 12c.

The control handle unit 12b is provided with the angle knob 12e, a mode switch (SW) 13a, a zoom operating section 13b, a still image capture switch (not shown), and the like. The mode SW 13a is operated to switch between observation modes. The endoscope system 10 has a normal mode and a special mode as the observation modes. In the normal mode, a natural-colored image (hereinafter referred to as the normal image) of an object of interest (hereinafter referred to as the object) irradiated with white light, being the illumination light, is captured and displayed on the monitor 18. In the special mode, an image signal generated by imaging the object is used to extract blood vessels located at a specific depth from the blood vessels included in the object and an image of the extracted blood vessels is displayed on the monitor 18.

The processor device 16 is electrically connected to the monitor 18 and the console 19. The monitor 18 outputs image(s) of the object, information associated with the corresponding image(s), and the like. The console 19 functions as a UI (user interface), which receives input operation such as setting a function. Note that an external storage unit (not shown) for recording the images and the image information may be connected to the processor device 16.

Figure 2:
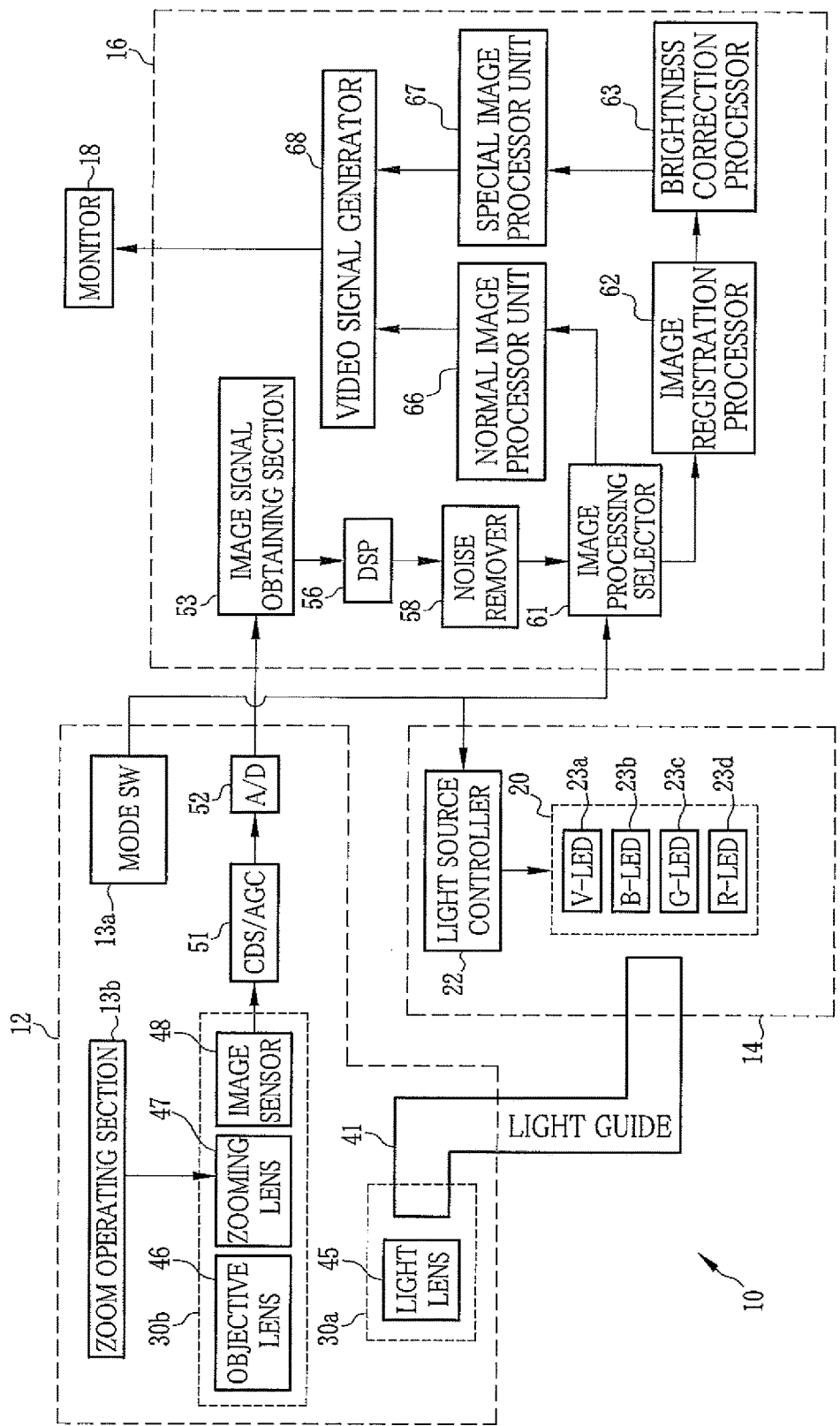
FIG. 2 is a block diagram illustrating functions of the endoscope system.
Figure 3:
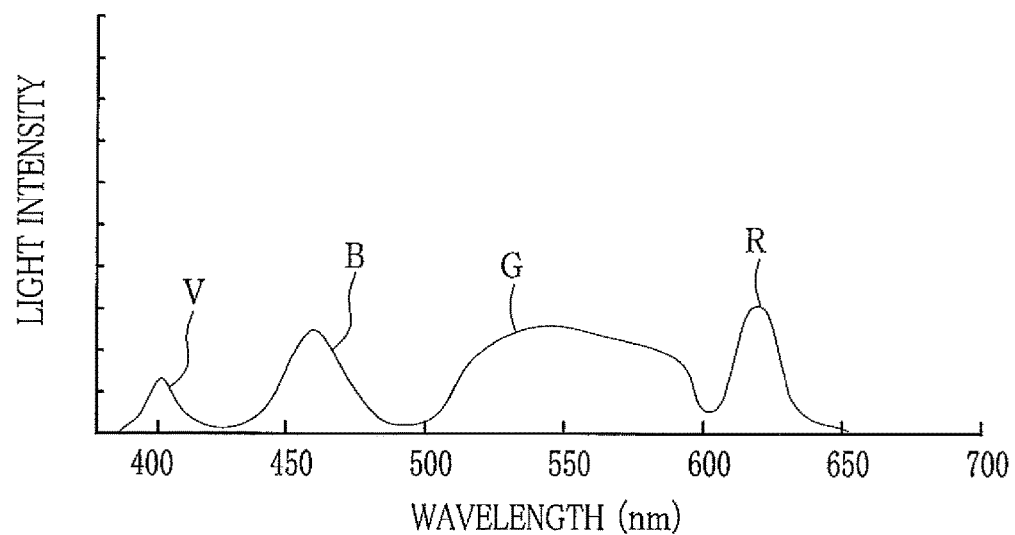
FIG. 3 is a graph illustrating optical spectrums of violet light, blue light, green light, and red light.

As illustrated in FIG. 2, the light source device 14 comprises a light source unit 20 and a light source controller 22 for controlling the light source unit 20. The light source unit 20 comprises, for example, two or more semiconductor light sources and generates the illumination light to be applied to the object. In this embodiment, the light source unit 20 comprises LEDs of four colors: a V-LED (Violet Light Emitting Diode) 23a, a B-LED (Blue Light Emitting Diode) 23b, a G-LED (Green Light Emitting Diode) 23c, and an R-LED (Red Light Emitting Diode) 23d. As illustrated in FIG. 3, the V-LED 23a is a violet semiconductor light source that emits violet light V in a wavelength range of 380 to 420 nm and having the center wavelength of 405 nm. The B-LED 23b is a blue semiconductor light source that emits blue light B in a wavelength range of 420 to 500 nm having the center wavelength of 460 nm. The G-LED 23c is a green semiconductor light source that emits green light G in a wavelength range of 480 to 600 nm. The R-LED 23d is a red semiconductor light source that emits red light R in a wavelength range of 600 to 650 nm and having the center wavelength 620-630 nm. Note that each of the center wavelength of the V-LED 23a and the center wavelength of the B-LED 23b has a width in the order of ±5 nm to ±10 nm.

Turning on and off of the LEDs 23a to 23d, the light emission amounts, and the like are controlled independently by the light source controller 22 through inputting the corresponding control signals. In the normal mode, the light source controller 22 turns on all of the V-LED 23a, the B-LED 23b, the G-LED 23c, and the R-LED 23d. The white light that includes the violet light V, the blue light B, the green light G, and the red light R is used as the illumination light in the normal mode. In the special mode, the light source controller 22 controls the light source unit 20 to perform a first emission mode and a second emission mode sequentially. In the first emission mode, the light source controller 22 turns on only the V-LED 23a and turns off the remaining LEDs 23b to 23d. In the second emission mode, the light source controller 22 turns off the V-LED 23b and turns on only the B-LED 23b and keeps the remaining LEDs (the V-LED 23a and the like) turned off. In other words, the violet light V and the blue light B are generated in this order and applied to the object. In this embodiment, the violet light V is the first illumination light. In this embodiment, the blue light B is the second illumination light that differs in wavelength range from the first illumination light and has wavelengths longer than the first illumination light.

In the special mode in this embodiment, the violet light V from the V-LED 23a and the blue light B from the B-LED 23b are used as the first illumination light and the second illumination light, respectively, as described above. An optical filter or the like that limits the wavelength range of the light may be provided in the light source unit 20. Thereby the violet light V and the blue light B, with their respective wavelength ranges limited, are applied as the illumination light for the special mode.

The blood vessels at a specific depth are extracted clearly in the case where the scattering coefficients of the object are different between the first and second illumination light and the absorption coefficients of hemoglobin are the same between the first and second illumination light. For example, the scattering coefficient of the object in each of the wavelength ranges of the illumination light correlates with the penetration depth into the object, that is, the depth of the blood vessels (under the mucosal surface) rendered observable by the illumination light of the corresponding wavelength range. The absorption coefficient of hemoglobin correlates with the blood vessel contrast of the blood vessels observed using each of the illumination light. The condition "the scattering coefficients of the object are different from each other and the absorption coefficients of hemoglobin are substantially the same" with respect to the first and second illumination light used in the special mode means that two types of light in different wavelength ranges are selected to render the blood vessels at the different depths under the mucosal surface observable at substantially the same contrast. The above-described condition may not be sufficiently satisfied depending on the characteristics (e.g. the center wavelength) or the like of the LEDs used in the light source unit 20. In this case, the first and second illumination light may be in their respective wavelength ranges between which at least the scattering coefficients of the object are different from each other and in which the absorption coefficients of hemoglobin are as close to each other as possible. Note that, in a case where the wavelength range of the first illumination light is on the shorter wavelength side than the second illumination light, "the scattering coefficients of the object differ from each other" means that a ratio of the scattering coefficient of the second illumination light to the scattering coefficient of the first illumination light is less than or equal to 0.8. The difference between the scattering coefficients of the first and second illumination light is greater than or equal to 70 ($cm^{-1}$), for example.

Figure 4:
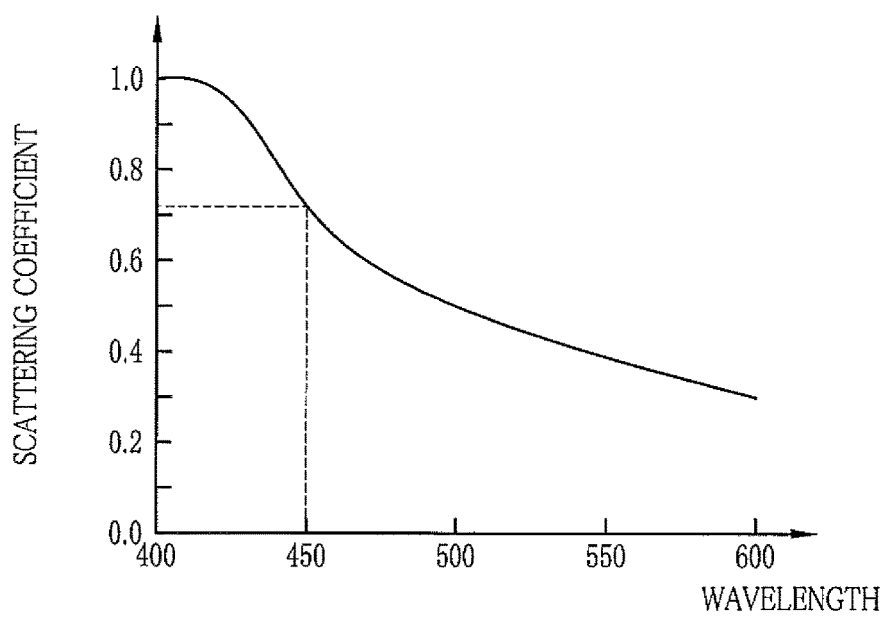
FIG. 4 is a graph of scattering coefficient of an object of interest.
Figure 5:
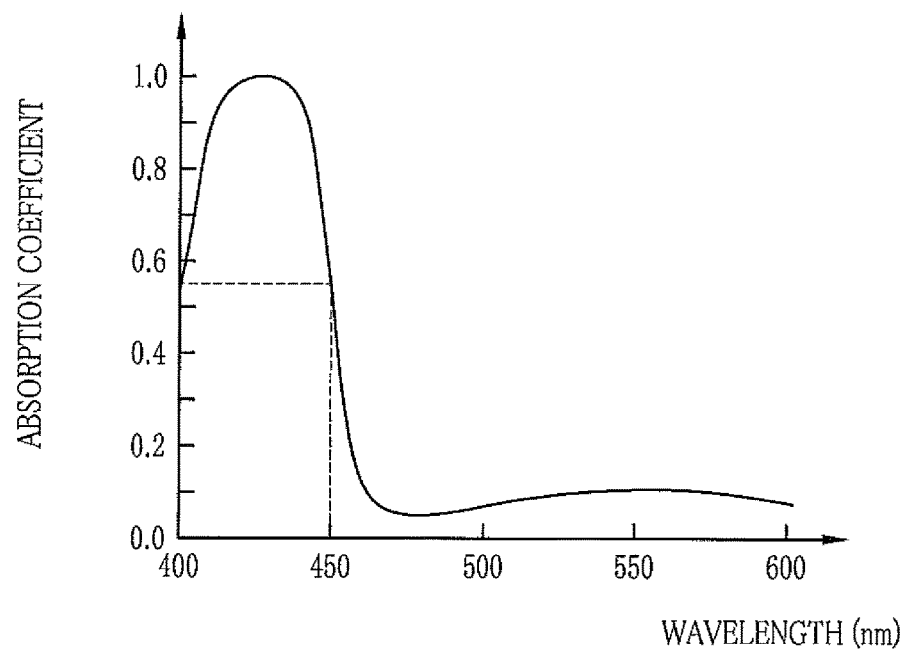
FIG. 5 is a graph of absorption coefficient of hemoglobin.

With regard to the violet light V and the blue light B, which are used as the illumination light in the special mode, a ratio of the scattering coefficient of the blue light B to the scattering coefficient of the violet light V is 0.75 as illustrated in FIG. 4. The blue light B and the violet light V have substantially the same absorption coefficient of hemoglobin (absorption coefficient of oxyhemoglobin: absorption coefficient of deoxyhemoglobin=3:7) as illustrated in FIG. 5.

The light of four colors from the respective LEDs 23a to 23d are incident on the light guide 41, which extends through the insertion section 12a, through a light path combiner (not shown) comprising a mirror, a lens, and the like. The light guide 41 extends through the endoscope 12 and a universal cord, which connects the endoscope 12 to the light source device 14 and the processor device 16. The light guide 41 transmits the illumination light, which is generated by the light source unit 20, to the distal portion 12d of the endoscope 12.

The distal portion 12d of the endoscope 12 comprises an illumination optical system 30a and an imaging optical system 30b. The illumination optical system 30a has a light lens 45. The illumination light transmitted through the light guide 41 is applied to the object through the light lens 45. The imaging optical system 30b has an objective lens 46, a zooming lens 47, and an image sensor (an imaging unit) 48. The light reflected from the object is incident on the image sensor 48 through the objective lens 46 and the zooming lens 47. An image of the light reflected from the object is formed on the image sensor 48. Note that the zooming lens 47 is moved as desired between the telephoto end and the wide angle end by operating the zoom operating section 13b, to magnify or reduce the size of the light image of the object formed on the image sensor 48.

The image sensor 48 is a color image sensor, which captures images of an object irradiated with the illumination light. Each pixel of the image sensor 48 is provided with an R (red) color filter, a G (green) color filter, or a B (blue) color filter shown in FIG. 6. The B pixel (the blue pixel) provided with the B color filter receives light from violet to blue. The G pixel (the green pixel) provided with the G color filter receives green light. The R pixel (the red pixel) provided with the R color filter receives red light. The R pixels, the G pixels, and the B pixels output image signals of R, G, and B colors, respectively. In the case where the emission mode of the light source unit 20 is in the first emission mode in the special mode, the violet light V is used as the illumination light. The image sensor 48 captures an image of the object irradiated with the violet light V. The B pixels of the image sensor 48 output a first image signal (hereinafter referred to as the B1 image signal) corresponding to the violet light V. In the case where the emission mode of the light source unit 20 is in the second emission mode, the blue light B is used as the illumination light. The image sensor 48 captures an image of the object irradiated with the blue light B. The B pixels of the image sensor 48 output a second image signal (hereinafter referred to as the B2 image signal) corresponding to the blue light B.

A CCD (Charge Coupled Device) image sensor or a CMOS (Complementary Metal-Oxide Semiconductor) image sensor may be used as the image sensor 48. A complementary color image sensor with complementary color filters of C (cyan), M (magenta), Y (yellow), and G (green) may be used instead of the image sensor 48 of primary colors. In the case where the complementary color image sensor is used, CMYG image signals of four colors (CMYG) are outputted. The CMYG image signals of four colors are converted into the RGB image signals of three colors through complementary color-primary color conversion. Thereby the RGB image signals similar to or the same as those generated by the image sensor 48 are obtained. A monochrome sensor with no color filters may be used instead of the image sensor.

The CDS/AGC circuit 51 performs correlated double sampling (CDS) and automatic gain control (AGC) on an analog image signal obtained from the image sensor 48. The image signal that has passed through the CDS/AGC circuit 51 is converted into a digital image signal by an A/D (Analog to digital) converter 52. After the A/D conversion, the digital image signal is inputted to the processor device 16.

The processor device 16 comprises an image signal obtaining section 53, a DSP (Digital Signal Processor) 56, a noise remover 58, an image processing selector 61, a normal image processor unit 66, a special image processor unit 67, and a video signal generator 68. The image signal obtaining section 53 obtains a digital image signal from the image sensor 48 through the CDS/AGC circuit 51 and the A/D converter 52.

The DSP 56 performs various types of image processing such as defect correction process, offset processing, gain correction process, linear matrix processing, gamma conversion process, demosaicing process, and the like on the image signal obtained. In the defect correction process, signals of defective pixels of the image sensor 48 are corrected. In the offset processing, dark current components are removed from the image signals that have been subjected to the defect correction process. Thereby an accurate zero level is set. In the gain correction process performed after the offset processing, a signal level is adjusted or corrected by multiplying the image signals by a specific gain.

After the gain correction process, the image signals are subjected to the linear matrix processing to increase color reproducibility. Thereafter, brightness and saturation are adjusted or corrected through the gamma conversion process. After the gamma conversion process, the demosaicing process (also referred to as equalization process or synchronization process) is performed to generate signal(s) of color(s) lacking in each pixel through interpolation. Owing to the demosaicing process, each pixel has three colors (RGB) of signals. The noise remover 58 performs a noise removing process (for example, moving average method or median filter method) on the image signal that has been subjected to the demosaicing process performed by the DSP 56. The image signal from which the noise has been removed is transmitted to the image processing selector 61. In a case where the observation mode is set to the normal mode by operating the mode SW 13a, the image processing selector 61 transmits the RGB image signals to the normal image processor unit 66. In a case where the observation mode is set to the special mode by operating the mode SW 13a, the image processing selector 61 transmits the RGB image signals to the special image processor unit 67.

The normal image processor 66 operates in a case where the observation mode is set to the normal mode, and performs a color conversion process, a color enhancement process, and a structure enhancement process on the received image signal to generate the normal image signal. The color conversion process is performed on the RGB image signals through 3×3 matrix processing, a tone conversion process, a three-dimensional LUT (lookup table) process, and the like. The color enhancement process is performed on the image signals that have been subjected to the color conversion process. The structure enhancement process is to enhance the structure of the object (e.g. surface blood vessels, pit patterns, or the like). The structure enhancement process is performed on the image signals after the color enhancement process. As described above, the normal image is a color image produced from normal image signals that have been subjected to the various types of image processing all the way up to the structure enhancement process.

The special image processor unit 67 is a processor unit that operates in the case where the observation mode is set to the special mode. The special image processor unit 67 extracts the blood vessels located at a specific depth and produces (generates) an image in which the extracted blood vessels are displayed in colors different from the colors of the remaining blood vessels, with the use of the B1 image signal corresponding to the violet light V and the B2 image signal corresponding to the blue light B. The B1 image signal and the B2 image signal are inputted to the special image processor unit 67 through an image registration processor 62 and a brightness correction processor 63.

The image registration processor 62 performs registration between the object represented by the B1 image signal and the object represented by the B2 image signal. The B1 image signal and the B2 image signal are obtained sequentially. The image registration processor 62 corrects at least one of the B1 image signal and the B2 image signal.

The brightness correction processor 63 corrects the brightness of at least one of the B1 image signal and the B2 image signal that have been subjected to the registration performed by the image registration processor 62 so as to achieve a specific brightness ratio between the B1 image signal and the B2 image signal. To be more specific, since the light quantity ratio of the violet light V in the first emission mode and the light quantity ratio of the blue light B in the second emission mode are known, the gain correction is performed based on these light quantity ratios to achieve the brightness values obtained by applying the violet light V and the blue light B, respectively, of the same light quantity to the object. In other words, the gain correction is performed to make the brightness of the B1 image signal equal to the brightness of the B2 image signal.

Figure 7:
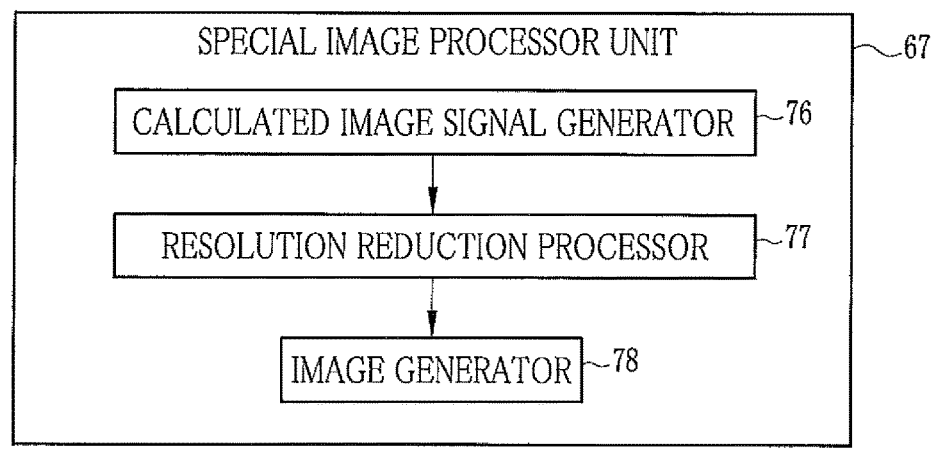
FIG. 7 is a block diagram illustrating functions of a special image processor unit.

As illustrated in FIG. 7, the special image processor unit 67 comprises a calculated image signal generator 76, a resolution reduction processor 77, and an image generator 78.

The calculated image signal generator 76 performs calculation(s) using the B1 image signal and the B2 image signal that have been subjected to the registration process and the brightness correction process. Thereby a calculated image signal is generated. To be more specific, the calculated image signal generator 76 calculates a difference or a ratio between the B1 image signal and the B2 image signal. In this embodiment, the calculated image signal generator 76 performs log conversion on the B1 image signal and the B2 image signal, and then generates a calculated image signal ΔB based on the difference between the B1 image signal and the B2 image signal that have been subjected to the log conversion. More specifically, the B1 image is subtracted from the B2 image signal to generate the calculated image signal ΔB. In a case where the B1 image signal and the B2 image signal are used without the log conversion, the ratio between the B1 image signal and the B2 image signal is calculated on a pixel-by-pixel basis to generate the calculated image signal. The B1 image signal and the B2 image signal have pixel values, which are proportionate to the amounts of light received by the corresponding pixels, respectively. Owing to the log conversion, the converted pixel values are proportionate to the corresponding concentration (density) values. Thus the results of the calculations become stable irrespective of the luminance (illumination) level of the illumination light used for generating each image signal.

Figure 8:
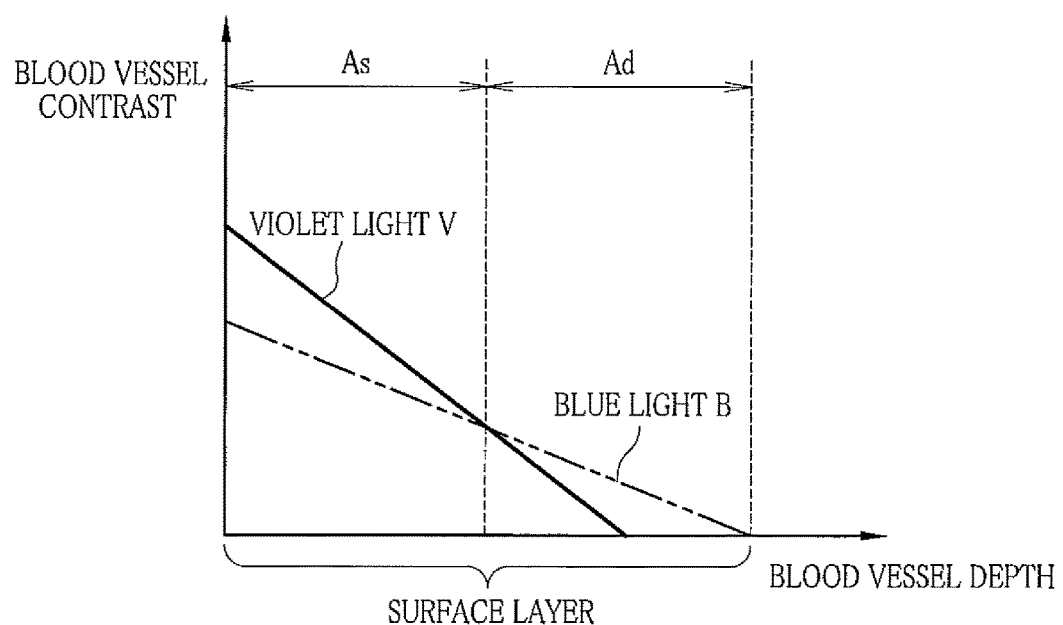
FIG. 8 is a graph schematically illustrating the relationship between the blood vessel depth and the blood vessel contrast.

To calculate the calculated image signal ΔB is to extract blood vessels located at a specific depth under the mucosal surface. For example, as illustrated in FIG. 8, the violet light V and the blue light B, which are used as the illumination light, render the surface blood vessels (the blood vessels located at the depths As and Ad) observable. The violet light V has the wavelengths shorter than those of the blue light B, so that the penetration depth into the object is small. Accordingly, the violet light V allows imaging the blood vessels located in a shallow position "As" under the mucosal surface, relative to the depth of the blood vessels imaged using the blue light B. However, the blood vessel contrast (the ratio of the amount of light reflected from the blood vessels to the amount of light reflected from the surrounding mucosa) of the blood vessels located in the shallow position As obtained by using the violet light is greater than that obtained by using the blue light B. The blue light B has the wavelengths longer than those of the violet light V, so that the penetration depth into the object is large. Accordingly, the blue light B allows imaging the blood vessels located in a deep position "Ad" under the mucosal surface, relative to the depth of the blood vessels imaged using the violet light V. However, the blood vessel contrast of the blood vessels located in the shallow position As obtained by using the blue light B is lower than that obtained by using the violet light V. In a case where the B1 image signal, which corresponds to the violet light V, is subtracted from the B2 image signal, which corresponds to the blue light B, the pixel representing the superficial blood vessels located in the shallow portion As under the mucosal surface has a high pixel value (white color) and the pixel representing the surface blood vessels located in the deep position Ad, which are deeper than the superficial blood vessels, has a low pixel value (black color).

The resolution reduction processor 77 is a so-called low pass filter (hereinafter referred to as the LPF) and reduces the resolution of the calculated image signal ΔB (resolution reduction process), which is generated by the calculated image signal generator 76. The magnitude of the resolution reduction process to be performed on the calculated image signal ΔB by the resolution reduction processor 77 is determined by a cutoff frequency of the LPF. The cut off frequency of the LPF is determined in advance at least to reduce the resolution of the calculated image signal ΔB.

Figure 9:
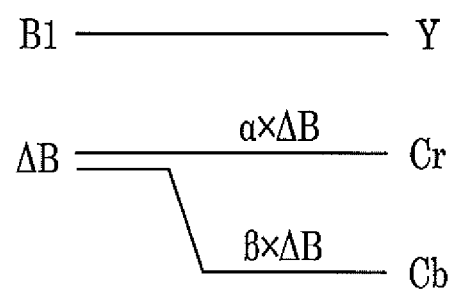
FIG. 9 is an explanatory view illustrating a method for generating a specific depth vessel-enhanced image.

The image generator 78 generates an image having two or more output channels from the calculated image signal ΔB that has been subjected to the resolution reduction process and one of the B1 image signal and the B2 image signal that are received by the special image processor unit 67. To be more specific, the image generator 78 generates an image having a luminance channel Y and chrominance channels Cb and Cr, which are related to color difference. The image generator 78 assigns one of the B1 image signal and the B2 image signal to the luminance channel Y and assigns the calculated image signal ΔB that has been subjected to the resolution reduction process to the chrominance channels Cb and Cr, thereby generating an image (hereinafter referred to as the specific depth vessel-enhanced image) in which a running pattern of the blood vessels located at a specific depth is enhanced in color. In this embodiment, the B1 image signal is assigned to the luminance channel Y to distinguish the superficial blood vessels from the surface blood vessels and to enhance the superficial blood vessels distinguished. As illustrated in FIG. 9, the B1 image signal, which corresponds to the light (the violet light V) of the relatively shorter wavelengths and in which the contrast of the superficial blood vessels is high, is assigned to the luminance channel Y. The calculated image signal ΔB is assigned to the chrominance channels Cb and Cr. In this case, the calculated image signal ΔB is multiplied by a coefficient α to be assigned to the chrominance channel Cb. The calculated image signal ΔB is multiplied by a coefficient β to be assigned to the chrominance channel Cr. These multiplications are performed to adjust the colors in the specific depth vessel-enhanced image with those in the image in which the surface blood vessels or the like are enhanced, displayed by the endoscope system.

More specifically, a conventional endoscope system having the special mode for enhancing the surface blood vessels captures an image of an object irradiated with narrowband blue light to generate a B image signal and captures an image of the object irradiated with narrowband green light to generate a G image signal. The B image signal is assigned to a B (blue) channel and a G (green) channel of an image to be displayed. The G image signal is assigned to an R (red) channel. Thereby the subsurface (medium depth and deep) blood vessels located in deep positions are enhanced and displayed in green (cyan) colors and the surface blood vessels located in the shallow position are enhanced and displayed in red (magenta) colors in the image. In ITU-R.601 standard, the relationships among the RGB image signals, the luminance channel Y, and the chrominance channels Cb and Cr are represented by the following expressions (1), (2), and (3).

$$Y=0.299R+0.587G+0.114B \quad (1)$$

$$Cb=-0.169-0.331G+0.5G \quad (2)$$

$$Cr=0.5R-0.419G-0.081B \quad (3)$$

"G" is substituted for "R" and "B" is substituted for "G" in the expressions (2) and (3), which represent the chrominance channels Cb and Cr. Thereby the chrominance channels Cb and Cr are expressed using (G−B) as shown in the expressions (4) and (5).

$$Cb=-0.169G+0.169B=0.169(G-B) \quad (4)$$

$$Cr=0.5G-0.5B=0.5(G-B) \quad (5)$$

In this embodiment, the superficial blood vessels are extracted and displayed, so that the calculated image signal ΔB is used in place of the (G−B) signal. More specifically, the calculated image signal ΔB is multiplied by the coefficient α=0.169 and then assigned to the chrominance channel Cb. The calculated image signal ΔB is multiplied by the coefficient β=0.5 and then assigned to the chrominance channel Cr. Thereby the endoscope system 10 displays the image of the coloration substantially the same as that displayed by the conventional endoscope system. Depending on a setting or the like, another coefficient may need to be multiplied to each of the coefficients α and β to further enhance the difference in color between the superficial blood vessels and the surface blood vessels, which are located in a relatively deep position.

Note that, in order to generate the specific depth vessel-enhanced image of the RGB colors from the luminance channel Y and the chrominance channels Cb and Cr, the following expressions (6), (7), and (8) are used for the inverse transformation in accordance with the ITU-R.601 standard.

$$R=Y+1.402Cr \quad (6)$$

$$G=Y-0.344Cb-0.714Cr \quad (7)$$

$$B=Y+1.772Cb \quad (8)$$

The normal image generated by the normal image processor unit 66 and the specific depth vessel-enhanced image generated by the special image processor unit 67 are inputted to the video signal generator 68. The video signal generator 68 converts the normal image and the specific depth vessel-enhanced image into video signals, which renders the images displayable on the monitor 18. The monitor 18 displays the normal image and/or the specific depth vessel-enhanced image based on the corresponding video signal(s).

Figure 10:
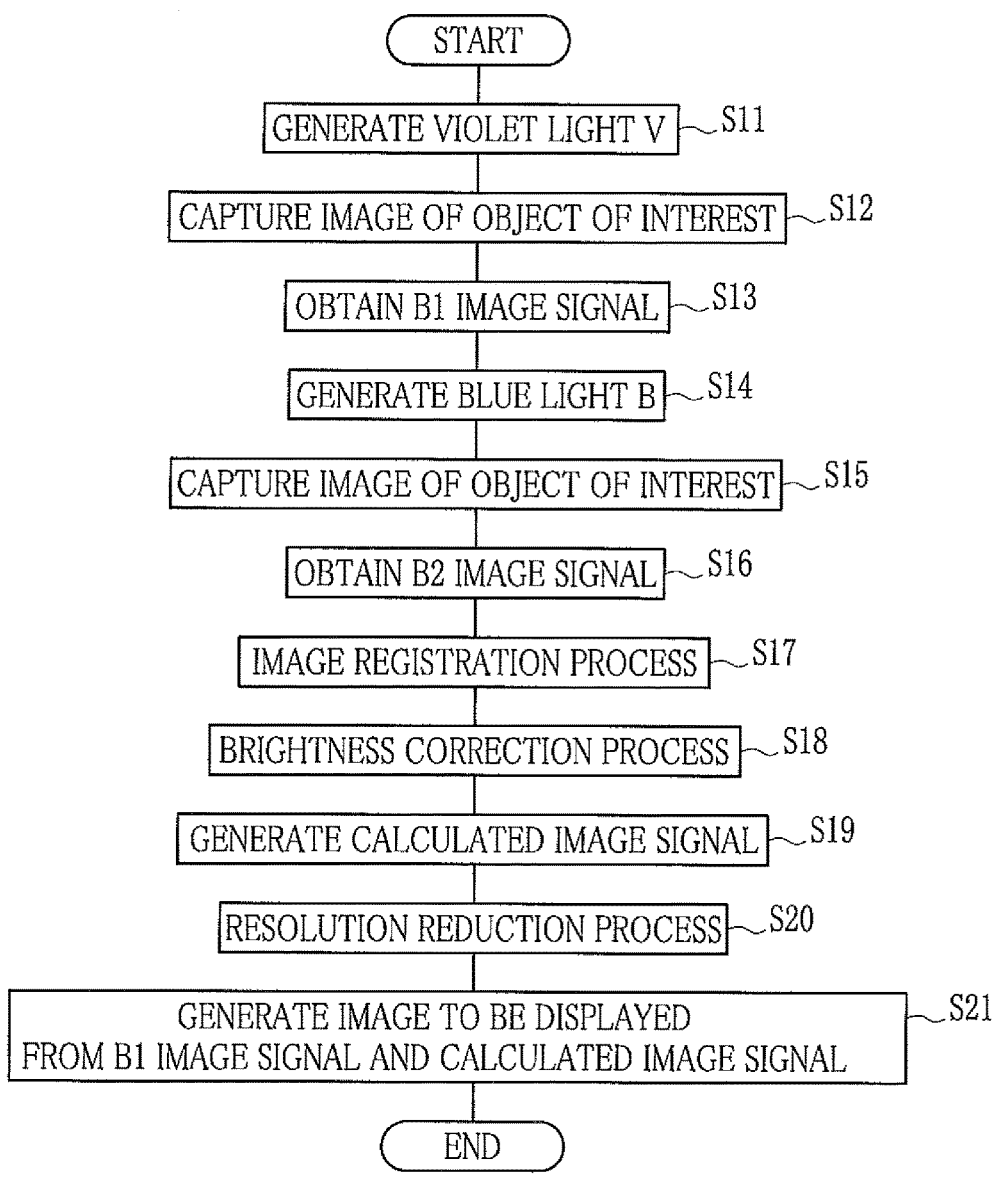
FIG. 10 is a flowchart illustrating steps in a special mode.
Figure 11:
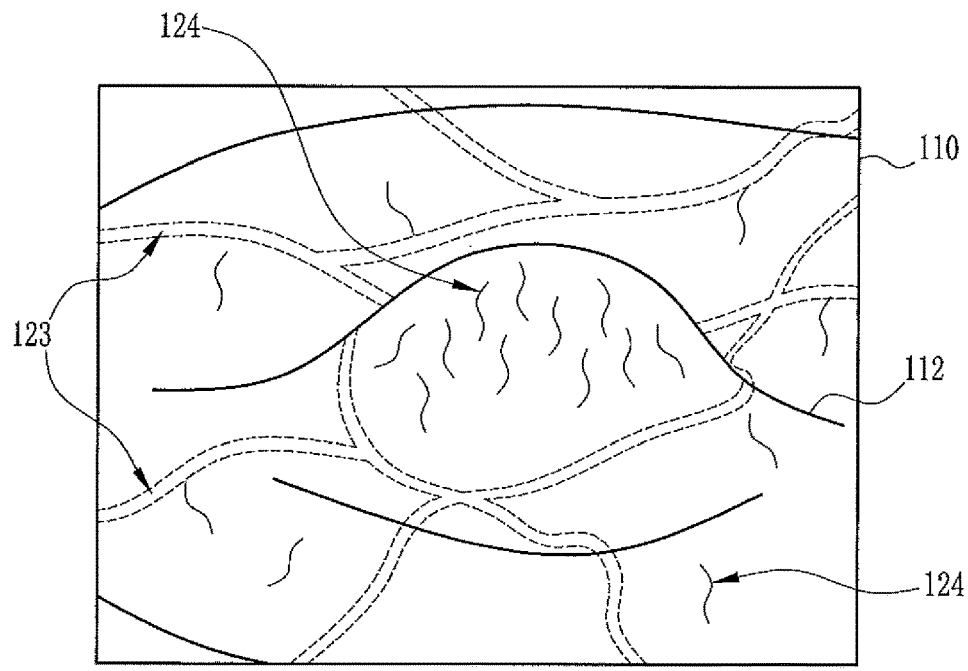
FIG. 11 is a schematic view of a B1 image signal.

Hereinafter, referring to FIG. 10, the steps of image processing in the special mode are described. First, the light source unit 20 generates the violet light V and applies the violet light V to the object (S11). The image sensor 48 images the object irradiated with the violet light V (S12). The image signal obtaining section 53 obtains the B1 image signal corresponding to the violet light V (S13). As illustrated in FIG. 11, a B1 image signal 110 is an image signal generated by imaging the object irradiated with the violet light V, so that a form 112 such as a protrusion on the object and superficial blood vessels 124 are rendered observable. The B1 image signal 110 also renders surface blood vessels 123, which are located deeper than the superficial blood vessels 124, observable.

Figure 12:
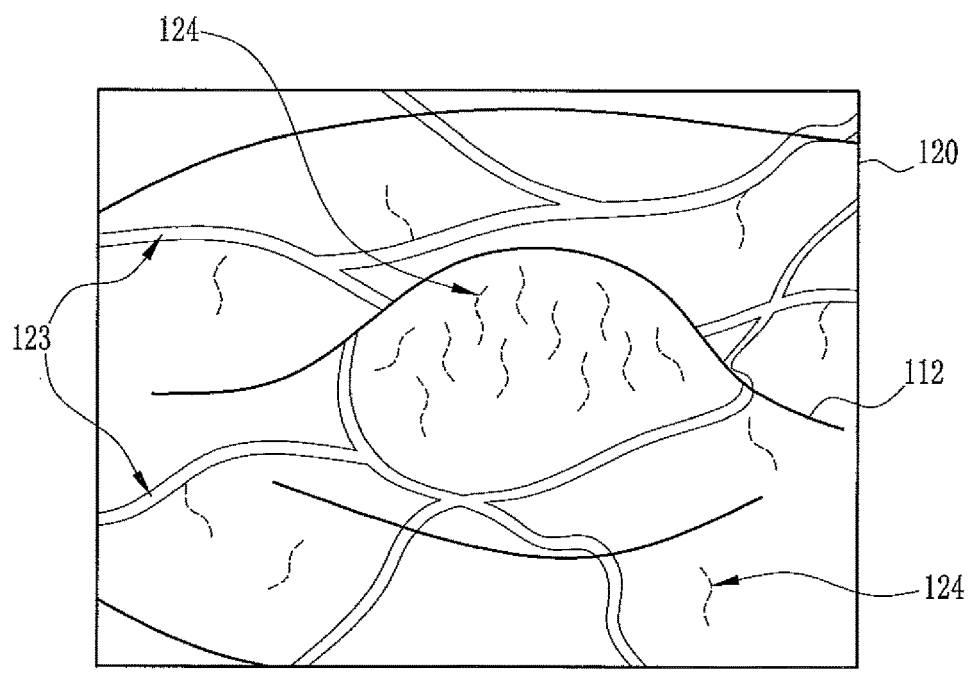
FIG. 12 is a schematic view of a B2 image signal.

Next, the light source unit 20 generates the blue light B and applies the blue light B to the object (S14). The image sensor 48 images the object irradiated with the blue light B (S15). The image signal obtaining section 53 obtains the B2 image signal corresponding to the blue light B (S16). As illustrated in FIG. 12, a B2 image signal 120 is an image signal generated by imaging the object irradiated with the blue light B, so that the form 112 of the object and the surface blood vessels 123, which are located in a relatively deep position, are rendered observable. The B2 image signal 120 also renders the superficial blood vessels 124 observable. In a case where the B1 image signal 110 is compared with the B2 image signal 120, the contrast of the superficial blood vessels 124 is higher in the B1 image signal 110. The contrast of the surface blood vessels 123, which are located deeper than the superficial blood vessels 124, is higher in the B2 image signal 120.

Figure 13:
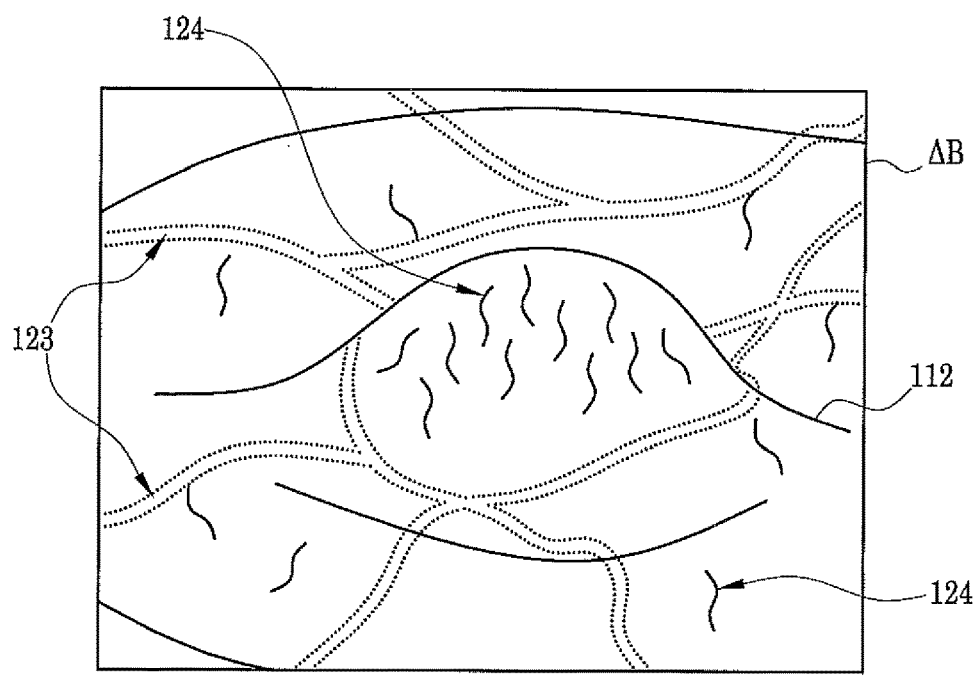
FIG. 13 is a schematic view of a calculated image signal.
Figure 14:
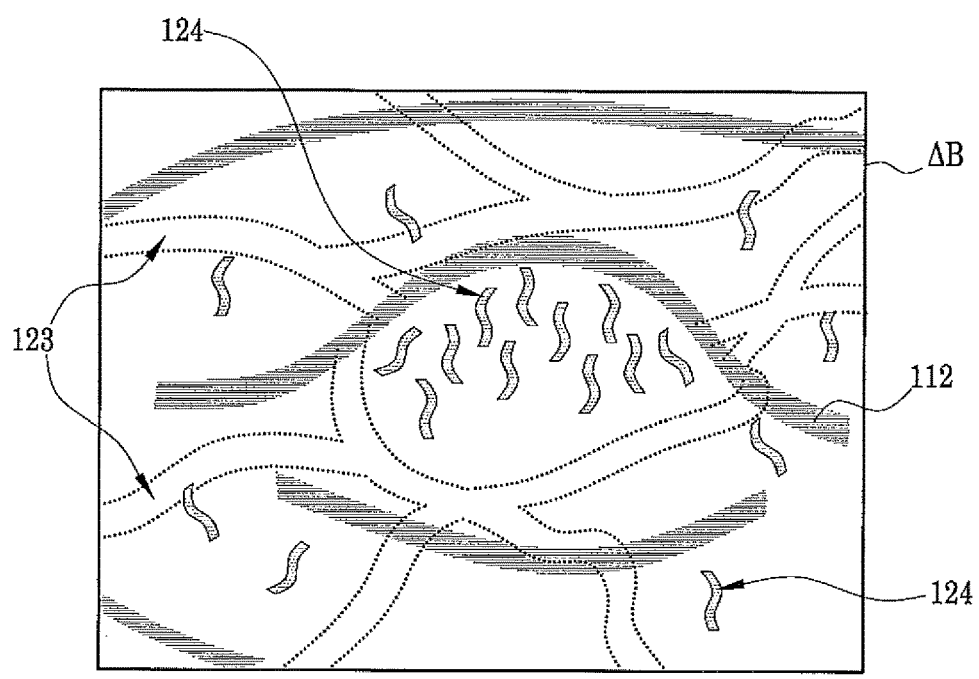
FIG. 14 is a schematic view of a calculated image signal after a resolution reduction process.

The image registration processor 62 performs the registration between the B1 image signal and the B2 image signal (S17), which are obtained as described above. Then the brightness correction processor 63 performs the brightness correction process (S18) on the B1 image signal and the B2 image signal. Thereafter, the B1 image signal and the B2 image signal are inputted to the special image processor unit 67. The calculated image signal generator 76 of the special image processor unit 67 generates the calculated image signal ΔB (S19). In the calculated image signal ΔB, the pixel values corresponding to the surface blood vessels 123, which are located in a relatively deep position, are low and the pixel values corresponding to the superficial blood vessels 124 are high, as compared with those in the original image signal (for example, the B1 image signal shown in FIG. 11 or the B2 image signal shown in FIG. 12). Accordingly, as illustrated in FIG. 13, the difference between the superficial blood vessels 124 and the surface blood vessels 123, which are located in the relatively deep position, is more apparent than that in the original image signal. After the special image processor unit 67 generates the calculated image signal ΔB, the resolution reduction processor 77 of the special image processor unit 67 reduces the resolution of the calculated image signal ΔB (S20). As illustrated in FIG. 14, the surface blood vessels 123 and the superficial blood vessels 124 become blurred in the calculated image signal ΔB that has passed through the resolution reduction processor 77.

Figure 15:
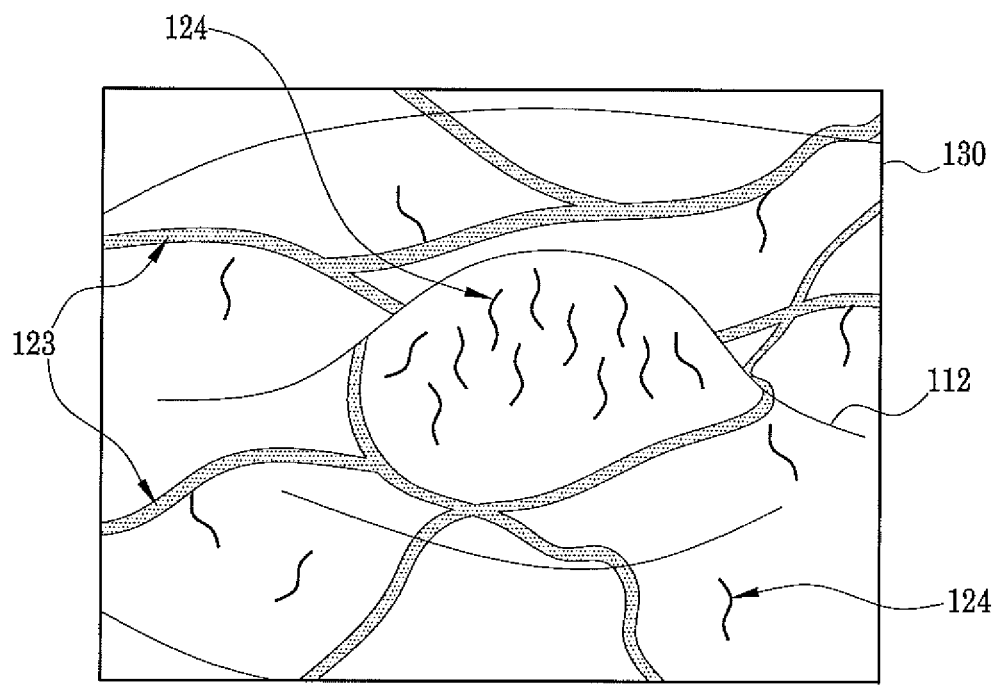
FIG. 15 is a schematic view of a specific depth vessel-enhanced image.

Thereafter, the image generator 78 of the special image processor unit 67 assigns the B1 image signal, in which the contrast of the superficial blood vessels 124 is high, to the luminance channel Y and assigns the calculated image signal ΔB, in which the resolution is reduced, to the chrominance channels Cr and Cb. Thereby the image generator 78 generates the specific depth vessel-enhanced image. As illustrated in FIG. 15, a specific depth vessel-enhanced image 130 shows the surface blood vessels 123 in the cyan color(s) and the superficial blood vessels 124 in the magenta color(s). Thus, the difference in color in the specific depth vessel-enhanced image 130 makes the superficial blood vessels 124 and the surface blood vessels 123 distinguishable from each other. Actually, the specific depth vessel-enhanced image 130 facilitates the observation of the superficial blood vessels 124.

As described above, the endoscope system 10 calculates the calculated image signal ΔB based on the difference (or the ratio) between the B1 image signal corresponding to the violet light V and the B2 image signal corresponding to the blue light B. The image signal in which the contrast of the blood vessels to be enhanced is high is assigned to the luminance channel Y. The calculated image signal ΔB is assigned to the chrominance channels Cb and Cr. Although it has been difficult to distinguish the superficial blood vessels 124 from the surface blood vessels 123 located deeper than the superficial blood vessels, the difference in color in the produced image makes the superficial blood vessels 124 visible and distinguishable from the surface blood vessels 123 and thus the blood vessels 123 and 124 are enhanced in the image.

Due to the difference in timing of obtaining the B1 image signal and the B2 image signal, a difference (or an error) between the B1 image signal, which is to be assigned to the luminance channel Y, and the calculated image signal ΔB may occur. This results in out-of-register colors or color shift in the specific depth vessel-enhanced image 130. To prevent this, in the endoscope system 10, the calculated image signal ΔB is assigned to the chrominance channels Cb and Cr, after the resolution of the calculated image signal ΔB is reduced by the resolution reduction processor 77. Thereby the color shift is reduced.

In the above embodiment, the image generator 78 assigns the B1 image signal, in which the contrast of the superficial blood vessels 124 is relatively high, to the luminance channel Y and assigns the calculated image signal ΔB to the chrominance channels Cb and Cr. Thereby the image generator 78 generates the specific depth vessel-enhanced image 130 that selectively enhances the superficial blood vessels 124. Note that the image generator 78 may generate a specific depth vessel-enhanced image that enhances the surface blood vessels 123 located in a relatively deep position. In this case, the calculated image signal generator 76 subtracts the B2 image signal from the B1 image signal after the log conversion, to generate the calculated image signal ΔB in a manner reverse to the above embodiment. In this case, the image generator 78 assigns the B2 image signal, in which the contrast of the surface blood vessels 123 is high, to the luminance channel Y and assigns the calculated image signal ΔB that is generated by subtracting the B2 image signal from the B1 image signal to the chrominance channel Cb and Cr. Thereby the image generator 78 generates the specific depth vessel-enhanced image.

The specific depth vessel-enhanced image 130 of this embodiment is capable of enhancing the superficial blood vessels 124 because the calculated image signal ΔB is generated by subtracting the B1 image signal from the B2 image signal. In this embodiment, the image generator 78 assigns the B1 image signal, in which the contrast of the superficial blood vessels 124 is high, to the luminance channel Y in generating the specific depth vessel-enhanced image 130 in which the superficial blood vessels 124 are to be enhanced. Alternatively, the specific depth vessel-enhanced image that enhances the superficial blood vessels 124 may be generated by assigning the B2 image signal to the luminance channel Y.

The image generator 78 may be capable of selecting which one of the B1 image signal and the B2 image signal is to be assigned to the luminance channel Y in generating the specific depth vessel-enhanced image. For example, the image generator 78 may be provided with a first mode, in which the B1 image signal is assigned to the luminance channel Y, and a second mode, in which the B2 image signal is assigned to the luminance channel Y. The image generator 78 is capable of producing an image in the mode selected from the first and second modes. In the case where the image signal is selectively assigned to the luminance channel Y, the image generator 78 may automatically select the image signal to be assigned to the luminance channel Y. For example, a comparison between the B1 image signal and the B2 image signal is performed and the image signal with less noise in the entire image signal or in a designated region of interest may be automatically assigned to the luminance channel Y. The image signal with higher contrast in the entire image signal or in a designated region of interest may be automatically assigned to the luminance channel Y.

Figure 16:
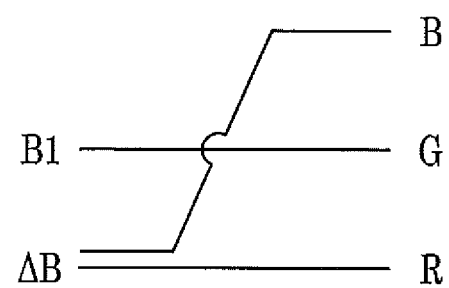
FIG. 16 is an explanatory view illustrating a modified example of a method for generating a specific depth vessel-enhanced image.

In the above embodiment, the image generator 78 assigns the B1 image signal to the luminance channel Y, and assigns the calculated image signal ΔB to the chrominance channels Cb and Cr. Thereby the image generator 78 produces the specific depth vessel-enhanced image 130 of a YCbCr format. Instead, an image of an RGB format may be produced. The image of the RGB format has an R channel, a G channel, and a B channel. In this case, as illustrated in FIG. 16, the image generator 78 assigns the B1 image signal to the G channel that most contributes to the brightness or luminance, and assigns the calculated image signal ΔB to the remaining channels, the B channel and the R channel.

Figure 17:
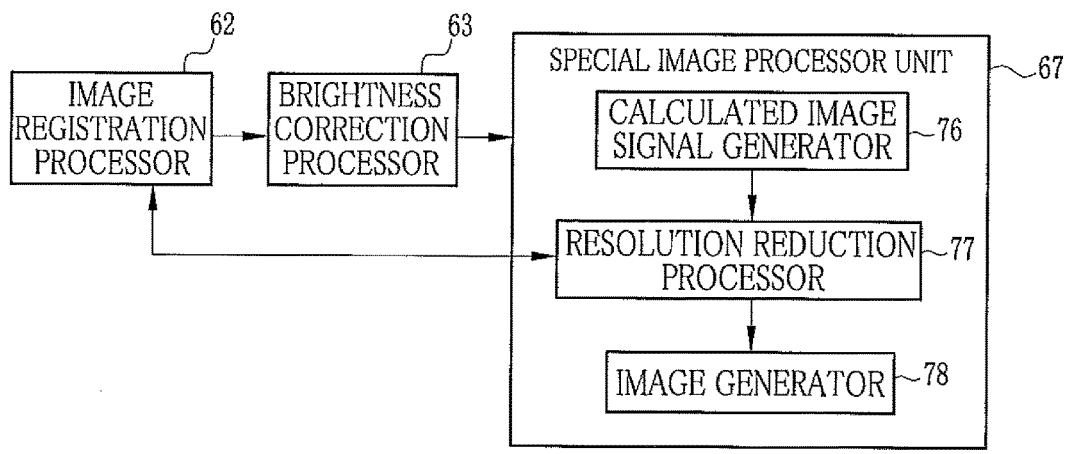
FIG. 17 is a block diagram illustrating a special image processor and an image registration processor working in conjunction with each other.

In the above embodiment, the cutoff frequency of the LPF to be used in the resolution reduction processor 77 is set in advance. Instead, the cutoff frequency of the LPF may be variable. In other words, the cutoff frequency of the LPF may be set dynamically. For example, as illustrated in FIG. 17, the image registration processor 62 inputs the accuracy (registration accuracy) of the registration between the B1 image signal and the B2 image signal to the resolution reduction processor 77. The resolution reduction processor 77 changes the cutoff frequency (the magnitude of the resolution reduction process) of the LPF in accordance with the registration accuracy inputted. More specifically, the cutoff frequency of the LPF is set to a higher frequency to reduce the magnitude of the resolution reduction process as the registration accuracy is increased. The cutoff frequency of the LPF is set to a lower frequency to increase the magnitude of the resolution reduction process as the registration accuracy decreases. Thereby the resolution reduction processor 77 optimally reduces the resolution of the calculated image signal ΔB and the blood vessels (for example, the superficial blood vessels 124) at a specific depth are properly enhanced and displayed.

Note that, in a case where the specific depth vessel-enhanced image is displayed or stored as a still image, the cutoff frequency of the LPF may be set within a range that preserves at least less than or equal to ⅛ of the Nyquist frequency, based on the resolution of the specific depth vessel-enhanced image to be produced.

In the above-described modified example, the resolution reduction processor 77 adjusts the magnitude of the resolution reduction process in accordance with the registration accuracy of the image registration processor 62. Conversely, the image registration processor 62 may adjust the registration accuracy in accordance with the magnitude of the resolution reduction process performed by the resolution reduction processor 77. In this case, the image registration processor 62 sets higher registration accuracy for the registration between the B1 and B2 image signals as the cutoff frequency of the LPF is increased and the magnitude of the resolution reduction process is reduced.

The registration accuracy for the registration between the B1 image signal and the B2 image signal, which is performed by the image registration processor 62, may be variable. The registration accuracy may be changed between the case in which the specific depth vessel-enhanced image, being the still image, is displayed or stored and the case in which a movie of the specific depth vessel-enhanced images is displayed. For example, in the case where the movie composed of the specific depth vessel-enhanced images is displayed on the monitor 18, the image registration processor 62 performs the registration between the B1 image signal and the B2 image signal at a first accuracy level that is lower than that in the case where the specific depth vessel-enhanced image is displayed (or stored) as a still image on the monitor 18. On the other hand, in the case where the specific depth vessel-enhanced image is displayed as a still image on the monitor 18, the image registration processor 62 performs the registration between the B1 image signal and the B2 image signal at a second accuracy level that is higher than that in the case where the movie of the specific depth vessel-enhanced images is displayed on the monitor 18. Thereby, in the case of displaying a movie, the specific depth vessel-enhanced images are produced at a high rate within a range in which the color shift is inconspicuous, and in the case of capturing a still image, in which the color shift is likely to become conspicuous, the specific depth vessel-enhanced image with no color shift is produced.

The image registration processor 62 may vary the registration accuracy for the registration between the B1 image signal and the B2 image signal, in accordance with the size of the specific depth vessel-enhanced image to be produced. For example, in a case where the specific depth vessel-enhanced image to be produced has a large size, a slight color shift may become conspicuous. In this case, the image registration processor 62 performs the registration with high accuracy. In a case where the specific depth vessel-enhanced image to be produced has a small size, the color shift is inconspicuous. In this case, the image registration processor 62 performs the registration with low accuracy. Conversely, the image registration processor 62 may perform the registration with low accuracy in the case where the specific depth vessel-enhanced image to be produced has a large size and perform the registration with high accuracy in the case where the specific depth vessel-enhanced image to be produced has a small size. Thereby the processing load of the processor device 16 is optimized.

As described above, the resolution reduction processor 77 changes the cutoff frequency of the LPF in accordance with the registration accuracy in the case where the image registration processor 62 changes the registration accuracy between displaying a movie and capturing a still image or in accordance with the size of the specific depth vessel-enhanced image. For example, in a case where the images generated by the image generator 78 are displayed as a movie (hereinafter referred to as "in displaying a movie"), the image registration processor 62 reduces the registration accuracy for the registration between the B1 image signal and the B2 image signal to be lower than the registration accuracy used in the case where the image generated by the image generator 78 is stored as a still image (hereinafter referred to as "in obtaining a still image"). In this case, the resolution reduction processor 77 shifts the cutoff frequency of the LPF to be lower than that used in obtaining a still image (that is, the magnitude of the resolution reduction process is set to be higher than that used in obtaining a still image). In obtaining a still image, the image registration processor 62 sets the registration accuracy for the registration between the B1 image signal and the B2 image signal to be higher than the registration accuracy used in displaying a movie. In this case, the resolution reduction processor 77 shifts the cutoff frequency of the LPF to be higher than that used in displaying a movie (that is, the magnitude of the resolution reduction process is set to be lower than that used in displaying a movie). In other words, in displaying a movie, the LPF of the resolution reduction processor 77, which imposes a small processing load on the processor device 16, is given a higher priority. In obtaining a still image, accurate registration by the image registration processor 62 is given a higher priority.

Note that the image registration processor 62 may not perform the registration between the B1 image signal and the B2 image signal in the case where a movie is displayed. The image registration processor 62 may perform the registration between the B1 image signal and the B2 image signal only in the case where still images are captured.

In the above embodiment, the resolution reduction processor 77 uses the LPF to reduce the resolution of the calculated image signal ΔB. Instead, the resolution of the calculated image signal ΔB may be reduced by scaling-down the calculated image signal ΔB and then scaling-up the calculated image signal ΔB to its original size. In this case, for example, an image scaling-down method that causes low aliasing in scaling-down the calculated image signal ΔB is used. For example, the resolution of the calculated image signal ΔB may be reduced by scaling-down the calculated image signal ΔB through area average method and then scaling-up the calculated image signal ΔB through cubic spline interpolation.

In the above embodiment, in the first emission mode, the violet light V is used as the illumination light. In the second emission mode, the blue light B is used as the illumination light. The two types of light that differ from each other in wavelength range, which are used in the special mode, may be in wavelength ranges different from the above. By changing the wavelength range(s), a specific depth vessel-enhanced image may be produced for blood vessels at any depths.

Figure 6:
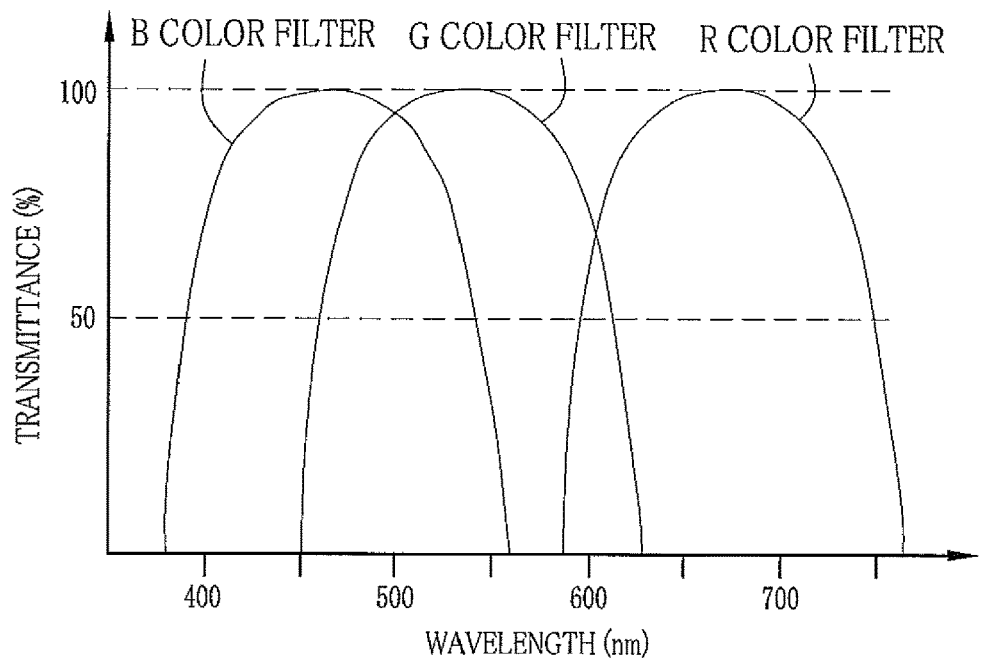
FIG. 6 is a graph of spectral characteristics of color filters.

The B color filter of the image sensor 48 is also sensitive to the green light G (see FIG. 6). The scattering coefficients of the object are different from each other and the absorption coefficients of hemoglobin are substantially the same between the light in the wavelength range receivable by the B pixels, of the reflection light and the like of the green light G, and the light in the wavelength range receivable by the G pixels, of the reflection light and the like of the green light G. For this reason, the only green light G may be used as the illumination light, for example. The broadband green light G includes the first illumination light and the second illumination light that are used in the special mode. A $B_G$ image signal, which is generated by imaging the object irradiated with the green light G and outputted from the B pixels, and a $G_G$ image signal, which is generated by imaging the object irradiated with the green light G and outputted from the G pixels are used in place of the B1 image signal and the B2 image signal of the above embodiment. In the case where the $B_G$ image signal and the $G_G$ image signal are used, for example, the subsurface blood vessels located in a relatively shallow position or a relatively deep position of the entire subsurface blood vessels may be selectively enhanced and displayed.

The R color filter of the image sensor 48 is also sensitive to the green light G (FIG. 6). The scattering coefficients of the object are different from each other and the absorption coefficients of hemoglobin are substantially the same between the light in the wavelength range receivable by the G pixels, of the reflection light and the like of the green light G, and the light in the wavelength range receivable by the R pixels, of the reflection light and the like of the green light G. For this reason, the light source unit 20 uses the broadband green light G as the illumination light. The broadband green light G includes the first illumination light and the second illumination light that are used in the special mode. A $G_G$ image signal (first image signal), which is generated by imaging the object irradiated with the green light G and outputted from the G pixels, and a $R_G$ image signal (second image signal), which is generated by imaging the object irradiated with the green light G and outputted from the R pixels are used in place of the B1 image signal and the B2 image signal of the above embodiment. In the case where the light source unit 20 generates the broadband illumination light (e.g. the green light G) that includes the first illumination light and the second illumination light, the image signal obtaining section 53 obtains the first image signal from the B pixels or the G pixels and obtains the second image signal from the G pixels or the R pixels.

The signals corresponding to the violet light V and the blue light B, which are received by the image sensor 48, may be compensated by using the property that the G color filter is also sensitive to the violet light V and the blue light B. For example, in the case where the violet light V is applied, a signal value corresponding to the violet light V is increased by adding a signal value obtained from the G pixel to a signal value obtained from the B pixel. In a like manner, in the case where the blue light B is applied, a signal value corresponding to the blue light B is increased by adding a signal value obtained from the G pixel thereto.

As described in the above embodiment, in the case where the superficial blood vessels 124 are distinguished from the surface blood vessels 123 and displayed, each of the wavelength ranges of the first illumination light and the second illumination light is within a range of up to (less than or equal to) 500 nm, for example. To be more specific, the violet light V having the center wavelength of 405±10 nm is used as the first illumination light and the blue light B having the center wavelength of 460±10 nm is used as the second illumination light as described in the above embodiment. The violet light having the center wavelength of 405±10 nm may be used as the first illumination light and the blue light having the center wavelength of 445±10 nm may be used as the second illumination light. The blue light having the center wavelength of 445±10 nm is generated from the blue light B by placing an optical filter that cuts the long wavelength component of the blue light B from the B-LED 23b in the light path of the blue light B from the B-LED 23b, for example. The B-LED 23b may be replaced with another LED that emits blue light having the center wavelength of 445±10 nm.

In a case where the subsurface (medium depth and deep) blood vessels are separated into the subsurface blood vessels located in a relatively shallow position and the subsurface blood vessels located in a relatively deep position and enhanced in the image, the wavelength range of each of the first illumination light and the second illumination light is greater than or equal to 500 nm, for example. To be more specific, the light having the center wavelength of approximately 500 nm is used as the first illumination light, for example. The light having the center wavelength of approximately 600 nm is used as the second illumination light, for example.

In the above-described embodiment, the calculated image signal generator 76 generates the calculated image signal ΔB, which represents the running pattern of the superficial blood vessels 124 located at a specific depth under the mucosal surface. Alternatively, note that the calculated image signal generator 76 may generate a calculated image signal D, which represents the blood vessel density, or a calculated image signal S, which represents an oxygen saturation level (hereinafter may referred to as the oxygen saturation level of blood vessels) of hemoglobin included in the blood vessels or the like.

The calculated image signal D, which represents the blood vessel density, is calculated using the calculated image signal ΔB of the above-described embodiment. For example, the calculated image signal ΔB of the above embodiment is an image signal showing the extracted superficial blood vessels 124 (see FIG. 13). A percentage of an area corresponding to the superficial blood vessels 124 in a unit area is calculated for each pixel, based on the calculated image signal ΔB. Thereby the calculated image signal D, which represents the blood vessel density of the superficial blood vessels 124, is generated. In this case, the image generator 78 assigns the B1 image signal to the luminance channel Y and assigns the calculated image signal D to the chrominance channels Cb and Cr. Thereby a blood vessel density image, which represents the blood vessel density of the superficial blood vessels 124, is produced. The blood vessel density image provides a direct suggestion to the diagnosis (e.g. the staging) of the Barrett's adenocarcinoma.

The calculated image signal S, which represents an oxygen saturation level of blood vessels, is generated by imaging the object irradiated with first blue light having the center wavelength of 445±10 nm, the green light G, and the red light R and by imaging the object irradiated with second blue light having the center wavelength of 473±10 nm, the green light G, and the red light R. The first blue light is generated from the blue light B, with the use of a first optical filter that limits the wavelength range of the blue light B from the B-LED 23$b$ such that the center wavelength of the first blue light is 445±10 nm. The first optical filter is an optical filter that cuts a long wavelength component of the blue light B, for example. The second blue light is generated from the blue light B, with the use of a second optical filter that limits the wavelength range of the blue light B from the B-LED 23$b$ such that the center wavelength of the second blue light is 473±10 nm. The second optical filter is an optical filter that cuts a short wavelength component of the blue light B, for example.

The above-described first blue light is in a wavelength range in which there is substantially no difference between the absorption coefficients of oxyhemoglobin and deoxyhemoglobin. The second blue light is in a wavelength range in which the absorption coefficient of oxyhemoglobin is different from that of deoxyhemoglobin. Accordingly, the ratio or the difference between the image signal generated by imaging the object irradiated with the first blue light and the image signal generated by imaging the object irradiated with the second blue light correlates with the oxygen saturation level. The correlation between the oxygen saturation level and the ratio or the difference, between the image signal corresponding to the first blue light and the image signal corresponding to the second blue light, is obtained in advance through experiments or the like, and the calculated image signal generator 76 stores the correlation in advance. The calculated image signal generator 76 calculates the ratio or the difference between the image signal corresponding to the first blue light and the image signal corresponding to the second blue light, and refers to the stored correlation to determine the oxygen saturation level, thereby generating the calculated image signal S. Each pixel of the calculated image signal S represents a value of the oxygen saturation level of the object. The image generator 78 generates the normal image signal from the image signals, which are generated by imaging the object irradiated with the first blue light, the green light G, and the red light, in a manner similar to the normal image processor unit 66. The normal image signal is assigned to the luminance channel Y. The calculated image signal S, which represents the oxygen saturation level, is assigned to the chrominance channels Cb and Cr. Thereby an oxygen saturation level image, which represents the oxygen saturation level of the object, is generated. The oxygen saturation image thus generated displays information, that is, the oxygen saturation level(s), useful for diagnosis.

Figure 18:
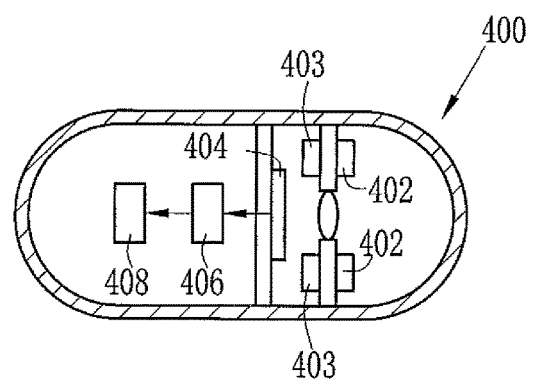
FIG. 18 is a schematic view of a capsule endoscope.

In the above embodiment, the implementation of the present invention is performed by using the endoscope system 10 comprising the endoscope 12 provided with the image sensor 48. The observation or examination is performed by inserting the endoscope 12 into a body cavity. The embodiments of the present invention are also suitable for a capsule endoscope system. For example, as illustrated in FIG. 18, the capsule endoscope system comprises at least a capsule endoscope 400 and a processor device (not shown).

The capsule endoscope 400 comprises a light source unit 402, a light source controller 403, an image sensor 404, a signal processor 406, and a transmission/reception antenna 408. The light source unit 402 is similar to the light source unit 20 of the above embodiment. The light source controller 403 controls the light source unit 402, in a manner similar to the above-described light source controller 22. The light source controller 403 is wirelessly communicable with the processor device of the capsule endoscope system through the transmission/reception antenna 408. The processor device of the capsule endoscope system is substantially similar to the processor device 16 of the above embodiment, except that the signal processor 406 has the functions of the normal image processor 66 and the special image processor 67. The vessel-enhanced image signal and the like generated by the signal processor 406 are transmitted to the processor device through the transmission/reception antenna 408. The image sensor 404 is similar to the image sensor 48 of the above embodiment.

Various changes and modifications are possible in the present invention and may be understood to be within the present invention.

What is claimed is:

1. An endoscope system comprising:
a light source unit for generating illumination light;
an image sensor for imaging an object of interest irradiated with the illumination light; and
an electric signal processor device configured for:
obtaining a first image signal and a second image signal from the image sensor, the first image signal corresponding to first illumination light of the illumination light, the second image signal corresponding to second illumination light of the illumination light, the second illumination light being different in wavelength range from the first illumination light;
generating a calculated image signal through calculation using the first image signal and the second image signal; and
generating an image in which one of the first image signal and the second image signal is assigned to a luminance channel or a green channel and the calculated image signal is assigned to a remaining channel,
wherein the electric signal processor device assigns the calculated image signal to two chrominance channels in a case where one of the first and second image signals is assigned to the luminance channel, and the electric signal processor device assigns the calculated image signal to a red channel and a blue channel in a case where one of the first and second image signals is assigned to the green channel.

2. The endoscope system according to claim 1, wherein the light source unit sequentially generates the first illumination light and the second illumination light having wavelengths longer than the first illumination light.

3. The endoscope system according to claim 1, wherein the electric signal processor device generates the calculated image signal that represents a running pattern of blood vessels located at a specific depth in the object, density of the blood vessels, or an oxygen saturation level of the blood vessels.

4. The endoscope system according to claim 3, wherein the electric signal processor device calculates a ratio or a difference between the first image signal and the second image signal to generate the calculated image signal.

5. The endoscope system according to claim 1, wherein the electric signal processor device is further configured for performing a resolution reduction process to reduce resolution of the calculated image signal, wherein
the electric signal processor device performs image generating by assigning assigns the calculated image signal with the resolution reduced by the resolution reduction to the remaining channel.

6. The endoscope system according to claim 5 wherein the electric signal processor device is further configured for correcting at least one of the first image signal and the second image signal and for performing registration between the object represented by the first image signal and the object represented by the second image signal,
wherein the electric signal processor device generates the calculated image signal from the first and second image signals in which the registration of the objects has been performed by the image registration processor.

7. The endoscope system according to claim 6, wherein the electric signal processor device performs resolution reduction by setting magnitude of the resolution reduction process in accordance with accuracy of the performed registration.

8. The endoscope system according to claim 7, wherein the electric signal processor device performs resolution reduction by reducing the magnitude of the resolution reduction process as the accuracy of the performed registration is increased.

9. The endoscope system according to claim 6, wherein the electric signal processor device performs image registration by setting accuracy of the registration in accordance with magnitude of the resolution reduction process.

10. The endoscope system according to claim 9, wherein the electric signal processor device performs image registration by increasing the accuracy of the registration as the magnitude of the resolution reduction process is reduced.

11. The endoscope system according to claim 6, wherein the electric signal processor device performs image registration by setting accuracy of the registration low and performs resolution reduction by setting magnitude of the registration reduction process high in a case where the generated image is displayed as a movie, as compared to the accuracy and the magnitude in a case where the generated image is displayed or stored as a still image.

12. The endoscope system according to claim 6, wherein the electric signal processor device performs image registration by setting accuracy of the registration high and performs resolution reduction by setting magnitude of the registration reduction process low in a case where the generated image is stored as a still image, as compared to the accuracy and the magnitude in a case where the generated image is displayed as a movie.

13. The endoscope system according to claim 1, wherein the electric signal processor device is further configured for correcting brightness of at least one of the first image signal and the second image signal, wherein
the electric signal processor device generates the image from the first or second image signal with the corrected brightness.

14. The endoscope system according to claim 1, wherein the electric signal processor device generates the image by assigning one of the first and second image signals with less noise to the luminance channel or the green channel.

15. The endoscope system according to claim 1, wherein the electric signal processor device generates the image by assigning one of the first and second image signals with higher contrast to the luminance channel or the green channel.

16. The endoscope system according to claim 1, wherein the electric signal processor device selectively performs image generating in a first mode, in which the first image signal is assigned to the luminance channel or the green channel, and a second mode, in which the second image signal is assigned to the luminance channel or the green channel.

17. The endoscope system according to claim 1, wherein the electric signal processor device generates the image by assigning the first image signal to the luminance channel or the green channel in a case where the first illumination light has wavelengths shorter than the second illumination light, and assigns the second image signal to the luminance channel or the green channel in a case where the second illumination light has wavelengths shorter than the first illumination light.

18. The endoscope system according to claim 1, wherein the center wavelength of the first illumination light is 405±10 nm and the center wavelength of the second illumination light is 445±10 nm.

19. A method for operating an endoscope system comprising the steps of:
generating illumination light with a light source unit;
imaging an object of interest irradiated with the illumination light, with an image sensor;
obtaining a first image signal and a second image signal from the image sensor, the first image signal corresponding to first illumination light of the illumination light, the second image signal corresponding to second illumination light of the illumination light, the second illumination light being different in wavelength range from the first illumination light;
generating a calculated image signal through calculation using the first image signal and the second image signal; and
generating an image in which one of the first image signal and the second image signal is assigned to a luminance channel or a green channel and the calculated image signal is assigned to a remaining channel,
wherein said method assigns the calculated image signal to two chrominance channels in a case where one of the first and second image signals is assigned to the luminance channel, and assigns the calculated image signal to a red channel and a blue channel in a case where one of the first and second image signals is assigned to the green channel.

* * * * *